United States Patent [19]

Drobník et al.

[11] Patent Number: 4,612,009

[45] Date of Patent: Sep. 16, 1986

[54] BIODEGRADABLE IMPLANT AND A METHOD FOR PREPARATION THEREOF

[75] Inventors: Jaroslav Drobník; Helena Stepánková, both of Prague, Czechoslovakia

[73] Assignee: Ceskoslovenska akademie Ved, Prague, Czechoslovakia

[21] Appl. No.: 743,518

[22] Filed: Jun. 11, 1985

[30] Foreign Application Priority Data

Jun. 19, 1984 [CS] Czechoslovakia ............... 4648-84

[51] Int. Cl.$^4$ .............................................. A61K 9/22
[52] U.S. Cl. ..................................... 604/891; 424/19
[58] Field of Search .................... 604/891, 890, 892; 424/14, 16, 19

[56] References Cited

U.S. PATENT DOCUMENTS

| | | | |
|---|---|---|---|
| 4,346,709 | 8/1982 | Schmitt | 604/891 |
| 4,351,337 | 9/1982 | Sidman | 604/891 |
| 4,450,150 | 5/1984 | Sidman | 604/891 X |

Primary Examiner—John D. Yasko
Attorney, Agent, or Firm—Leydig, Voit & Mayer, Ltd.

[57] ABSTRACT

The invention pertains to a biodegradable implant formed from a gel completely decomposable in body, which contains the antitumour medical - diamminedichloroplatinum addition compound (cisplatin) and to a method for preparation of this implant.

An object of the invention is a biodegradable implant, wherein a matrix of the said implant is formed by a starch gel containing 0.2 to 2 wt. % NaCl, plasticized by addition of 1 to 30 wt. % of glycerol, suitably shaped, and contains the homogeneously dispersed microcrystalline cisplatin in the amount of 1 to 15 wt. %.

A method for preparation the implant according to the invention consists in a homogeneous mixing of 1 wt. part of a viscous aqueous solution, obtained by dissolution of 0.4 to 4 wt. % NaCl and conversion of 1 to 6 wt. % of starch to a paste by boiling, with 0.1 to 0.8 wt. parts of glycerol, 0.5 to 1 wt. part of starch, and the required amount of microcrystalline cisplatin, deaeration of the mixture, conversion to a gel in a mould determining the final shape of implant by heating in a boiling-water bath, and, eventually, in hardening by soaking in a water-miscible solvent, advantageously in acetone or ethanol.

An advantage of the implant according to the invention consists in a relatively fast release of cisplatin into surroundings, which is desirable with respect to the mechanism of cisplatin action. Another advantage is the degradability of implant to products natural for body, which have not toxicologic nor immunologic importance.

2 Claims, No Drawings

BIODEGRADABLE IMPLANT AND A METHOD FOR PREPARATION THEREOF

The invention pertains to a biodegradable implant formed from a gel completely decomposable in body, which contains the antitumour medical—cis-diamminedichloroplatinum(II) addition compound (cisplatin), and to a method for preparation this implant.

The inorganic addition compound cis-diamminedichloroplatinum(II) (generic name cisplatin) proved useful in the clinical practice for treatment of several types of solid tumours. Similarly as other cytostatics, it has, in addition to its therapeutic properties, also undesirable side effects as nephrotoxicity, development of nausea and vomiting, and, in some cases, a damage of blood formation or some parts of nervous system. To overcome the nephrotoxicity, cisplatin is applied in practice in a considerable volume of physiologic saline or Ringer's solution as a long-termed intravenous infusion after the previous water supply to patient by infusion of a certain volume of glucose solution. This so called system application introduces cisplatin into the whole organism. Its advantage consists in the affliction of possible undetermined metastases, but, at the same time, the damage of numerous normal functions and development of the above mentioned side effects is disadvantageous.

The so called local application tries to overcome these disadvantages. Thus, for example, in a malignant affliction of bladder, the solution of cisplatin is introduced through a catheter directly into the bladder. In the treatment of ascitic forms of ovary tumours, the solution of cisplatin is introduced directly into peritoneum. If the tumour is not localized in the abdominal cavity, the cisplatin solution is introduced into an artery which supplies with blood the region afflicted with tumour. The last mentioned method has only limited use and numerous difficulties.

It is very difficult to treat tumours located in brain with cisplatin. The reason is an impermeable structure of walls of brain vessels which creates so called brain-blood barrier. This barrier causes that only a minute fraction of the system-applied cisplatin penetrates into the tissue of brain tumours.

It is known that the application of reservoirs with a semipermeable membrane, which are placed immediately on a tumour (Neoplasma 22, 313, 1975), represents a prospective method of local application of cytostatics. However, this method cannot be used for cisplatin with respect to its low solubility and instability of solutions. Rosenberg developed a degradable implant containing cisplatin and based on a matrix from a copolymer of lactac acid and glycolic acid. However, its disadvantage consists in rigidity and a slow diffusion of cisplatin into a tissue, which is undesirable from the point of view of the cisplatin mechanism of action.

The authors have found now that the local application of cisplatin can be realized by means of implants, if the microcrystalline cisplatin is homogeneously dispersed in a gel matrix and does not react with this matrix, neither with any kind of its decomposition products, and if the matrix is chosen in such a way that it rapidly releases cisplatin, possesses suitable mechanical properties and is gradually decomposed in body to products without toxicologic importance.

The invention pertains to a biodegradable implant, wherein a matrix of the said implant is formed by a starch gel, which contains 0.2-2 wt.% NaCl and is plasticized by addition of 1-30 wt.% of glycerol, is suitably shaped and contains the homogenously dispersed microcrystalline cisplatin in the amount of 1 to 15 wt.%.

The implant according to the invention is prepared by a procedure, wherein 1 wt. part of a viscous aqueous solution, obtained by dissolution of 0.4 to 4 wt.% NaCl and conversion of 1 to 6 wt.% of starch to a paste by boiling, is homogeneously mixed with 0.1 to 0.8 wt. parts of glycerol, 0.5 to 1 wt. part of starch, and the required amount of microcrystalline cisplatin, the mixture is deaerated, transferred into a gel in a mould determining the final shape of implant by heating in a boiling-water bath, and, eventually, hardened by soaking in a solvent miscible with water, advantageously in acetone or ethanol.

The method according to the invention is performed in several steps. In the first step, a viscous aqueous solution is prepared which contains 0.4 to 4 wt.% NaCl and 1 to 6 wt.% of starch converted into a paste by boiling. One wt. part of this viscous solution is cooled and mixed in the second step with 0.1 to 0.8 wt. parts of glycerol, 0.5 to 1 wt. part of starch and the required amount of microcrystalline cisplatin. The mixture is thoroughly homogenized. In the third step, the mixture is deaerated by the repeated application of vacuum with the action of ultrasound and transferred into a mould which determines the final shape of implant. The deaeration can be also carried out in the mould. In the fourth step, the mixture in mould is transferred into a gel by dipping the mould into a boiling-water bath for a suitable period of time (depending on the shape of mould). The implant is cooled and surface-hardened in the fifth step in a suitable bath, for example, in acetone or ethanol, whereas the degree of hardening depends from the required rigidity. It is then aseptically removed from the mould and adjusted to a suitable size and package. The implants may be sterilized with oxirane by a common technique and the residual oxirane has to be removed as soon as possible by the repeated and thorough application of vacuum. However, the sterilization is not necessary if a rough surface contamination is prevented. Bactericide properties of cisplatin provide the sterility of whole volume.

The implant is advantageous for a relatively fast release of cisplatin into surroundings, which is desirable with respect to the mechanism of cisplatin action. Another advantage consists in its degradability to products natural to body, which have not toxicologic nor immunologic importance. The implant is clearly visualized after application by X-ray due to the content of cisplatin and the release and spreading of cisplatin in surroundings may be evaluated from the changes of image contrast. The sterility of implant is secured by the bactericide capacity of cisplatin. The method of preparation is advantageous because, in addition to the shape, also rigidity of the implant may be controlled by time of hardening.

The invention is further illustrated in following examples:

EXAMPLE 1

Sodium chloride (0.1 g, pharmaceutical grade) was dissolved in 10 ml of distilled water and the solution was boiled with 0.3 g of wheat starch (Amylum tritici, pharmaceutical grade) under continuous stirring. To 7 g of the resulting viscous solution, it was added 3 g of glycerol (pharmaceutical grade), 5 g of starch (the same as above), and 0.5 g microcrystalline addition compound cis-diamminedichloroplatinum(II). The mixture is homogenized at least for 30 min, deaerated in a thick-walled flask exposed to an ultrasound field and five-times to vacuum, and transferred into a 20 cm$^3$ syringe. A silicone-rubber tube 30 cm long with I.D. 3 mm and wall thickness 0.5 mm, which was previously sterilized by steam and washed with acetone, was slided on the tip of syringe and fixed in the vertical position. The mixture was extruded into the tube ascendently by the rate approx. 10 cm/min. The tube was filled as much as to the last empty 15 mm, taken off the syringe and immersed into a boiling-water bath in such a way, that both ends protrude above the level, for 2 minutes. The tube was removed from the bath, stretched by a moderate tension in the vertical position and allowed to cool down. It was then placed in acetone for 7 hours in the same position under a moderate tension. The cylindric product with diameter about 2.8 mm spontaneously slipped out from the tube and was aseptically cut to suitable parts, which were placed in sterile ampoules and sealed. The content of platinum was determined in several randomly selected samples, which were measured and weighed. As a rule, 10 mg cisplatin corresponded to 30 mm of the cylinder length.

EXAMPLE 2

The mixture was prepared in the same way as in Example 1 till deaeration and poured into a pouch made by three-sided welding of two polyethylene foils of dimension 11×6 cm. The pouch was clamped in the vertical position between two flat parallel stainless-steel plates distanced 2.5 mm and the assembly was dipped for 4 minutes into a boiling-water bath. The assembly was cooled and immersed in acetone for 2 hours. Then, the stainless-steel plates were dismantled and the pouch was immersed in acetone for another 5 hours. The pouch was removed, acetone was allowed to evaporate in a sterile place, and the pouch was sealed on the open side. The required shapes may be cut with a sterile scalpel before application.

EXAMPLE 3

A plug prepared according to Example 1 had the diameter 2.3 mm and length 30 mm, was hardened for 7 h in acetone and contained 10 mg of cisplatin. It was placed in a medium through which passed physiologic saline (0.9% aqueous NaCl). The coefficient of diffusion $D = 0.112 \times 10^{-5}$ cm$^2$.s$^{-1}$ was determined from the kinetics of the decreasing content of cisplatin using the relationship for diffusion from a cylindric source into unlimited medium (J. Crank: The Mathematics of Diffusion, Claderon Press, Oxford 1957, p. 27-28). It follows that a half-time of cisplatin release is $T_{\frac{1}{2}} = 71$ min.

EXAMPLE 4

A plug of diameter 2.3 mm prepared according to Example 1 and hardened for 7 h in acetone was cut to 6 mm long sections. Two symmetrically placed spots were shaved on the back of male rats of Wistar breed. Next day, the animals were introduced into a light anaesthesia and a subcutaneous pocket was performed in the shaved places by a short cut and a probe. A weighed section of plug was introduced into the pocket and the wound was closed by a stitch. The implants were removed after 2, 4, 6, 8, 12 and 18 hours and the residual cisplatin was extracted into 0.9% aqueous NaCl solution and determined. The residues expressed as percent of the initial amount were as follows:

| hours | 2  | 4  | 6  | 8 | 12 | 18 |
|-------|----|----|----|---|----|----|
| %     | 92 | 35 | 18 | 5 | 0  | 0  |

EXAMPLE 5

Plugs prepared according to Example 1 were hardened for 7 hours in acetone. Their diameter was 2.3 mm and they contained 3.5 mg cisplatin per cm. Fifteen patients with brain tumors were chosen for the clinical testing, among them three cystic tumours (a cystic papilloma of choroid plexus, a glioblastoma, an anaplastic oligodendroglioma) and the remaining solid tumours: seventimes astrocytoma, threetimes metastasis (Grawitz's tumour of kidneys, melanoma, carcinoma of breast) and twice glioblastoma. The location and volume of tumours were determined by means of the computerized tomography; the histological type was determined by analysis of a sample obtained by biopsy. The plugs corresponding to the total dose of 5 to 15 mg cisplatin were introduced to the volume of tumour by the stereotactic method. In six cases, the tumour was surgically removed several weeks after the application of plugs. Two cases remained progressive and led to exits. The tissue obtained at autopsy was histologically investigated and platinum was determined in the section material by the neutron activation analysis. Results: Side-effects, as nausea, changes in the function of kidneys or blood count, have not been observed in any case. Changes of audiograms were found neither. Histologic investigations showed a colliquative necrosis in the neighbourhood of implant. Determinations of platinum three weeks after implantation in various distances from the implant showed that the concentration was higher than 8 ppm in the region of diameter 30 mm from the implant. The complete remission was observed after 6 months in the metastasis of melanoma and partial remissions in three tumours which did not exceed the volume of 5 cm$^3$.

We claim:

1. Biodegradable implant, wherein a matrix of the said implant is formed by a starch gel containing 0.2 to 2 weight percent of sodium chloride, plasticized by addition of 1 to 30 weight percent of glycerol, and suitably shaped, which contains a homogeneously dispersed microcrystalline cisplatin in the amount of 1 to 15 weight percent.

2. Method for preparation of the implant according to claim 1, wherein a viscous aqueous solution, obtained by dissolution 0.4 to 4 weight percent of sodium chloride and conversion of 1 to 6 weight percent of starch to a paste by boiling, is in the amount of one weight part homogeneously mixed with 0.1 to 0.8 weight parts of glycerol, 0.5 to 1 weight part of starch, and the required amount of microcrystalline cisplatin, the mixture is deaerated, transferred into a gel in a mould determining the final shape of implant by heating in a boiling-water bath, and, eventually, hardened by soaking in a solvent miscible with water, advantageously in acetone or ethanol.

* * * * *